United States Patent [19]
Collet et al.

[11] Patent Number: 5,962,722
[45] Date of Patent: Oct. 5, 1999

[54] α-HYDRAZINO ACID DERIVATIVES AND METHOD FOR MAKING SAME

[75] Inventors: André Collet; Joëlle Vidal; Jean-Christophe Hannachi, all of Lyons; Laure Guy, Villeurbanne, all of France

[73] Assignee: Centre National de la Recherche Scientifique, France

[21] Appl. No.: 09/029,628

[22] PCT Filed: Apr. 9, 1996

[86] PCT No.: PCT/FR96/01349

§ 371 Date: Mar. 3, 1998

§ 102(e) Date: Mar. 3, 1998

[87] PCT Pub. No.: WO97/09303

PCT Pub. Date: Mar. 13, 1997

[30] Foreign Application Priority Data

Sep. 7, 1995 [FR] France .................................. 95 10685

[51] Int. Cl.$^6$ ...................... C07C 205/06; C07C 243/14; C07D 209/18
[52] U.S. Cl. .............................. 560/29; 560/22; 562/439; 562/430; 564/148; 548/495; 548/496; 548/339.1
[58] Field of Search ...................................... 548/495, 496, 548/339.1; 562/439, 430; 564/148; 560/29

[56] References Cited

PUBLICATIONS

Database Caplus on STN, Acc. No. 1994:218456, Niederer et al., 'Amination with N–benzyloxycarbonyl–3–phenyloxaziridine as a route to sensitive chiral alpha–hydrazino acids: synthesis of L–hydrazino serine,' Tetrahedron Lett. 34(43), pp. 6859–6862, abstract 1993.
Vidal et al., 'Electrophilic amination: preparation and use of N–Boc–3–(4–cyanophenyl)oxaziridine, a new reagent that transfers a N–boc group to N– and C– nucleophiles,' J. Org. Chem. 58, pp. 4791–4793 1993.
Protective Groups in Organic Synthesis 2nd ed., Theodora Green and Peter Wuts, John Wiley & Sons, Inc, NY 1991.
Tetrahedron Letters, vol. 34, No. 43, pp. 6859–6862 (1993).
Tetrahedron Letters, vol. 31, pp. 2701–2704 (1975).
Chemical Abstracts, vol. 87, No. 1, (Jul. 4, 19977) Yamada, Shunichi et al.
J. Chemical Soc. Perkin Trans. 1 (1987), Lawton, Geoffrey et al.

Primary Examiner—Brian M. Burn
Assistant Examiner—Brian J. Davis
Attorney, Agent, or Firm—Wall Marjama Bilinski & Burr

[57] ABSTRACT

An α-hydrazino acid derivative of general formula (I) is described, wherein $R_1$, $R_2$, $R_3$ are hydrogen or a carbon radical, such that when $R_2$ and $R_3$ are different, C* is an asymmetric carbon of L, D or DL configuration, and $R_4$ and $R_5$ are a protecting group, characterized in that $R_4$ is a benzyl ArCH$_2$ radical of formula (a), wherein Ar is a phenyl radical or phenyl substituted by one or more X groups; X being hydrogen, halogen, a nitro or alkyl radical; and in that $R_5$ is a Y—O—CO group, where Y is a carbon radical different from $R_4$.

8 Claims, No Drawings

α-HYDRAZINO ACID DERIVATIVES AND METHOD FOR MAKING SAME

TECHNICAL FIELD

The invention relates, by way of new industrial products, to protected α-hydrazino acid derivatives; it also relates to a method for preparing such compounds.

PRIOR ART

α-Hydrazino acids are analogs of α-amino acids in which the amine functional group has been replaced with a hydrazine functional group.

When it is desired to use these α-hydrazino acids in synthesis, and in particular to incorporate them, in place of an amino acid, into the chain of a peptide in order to form either a hydrazino peptide —CO—NHNH—C— or an amino peptide —CO—N(NH$_2$)—C—, the presence of the two nitrogenous functional groups in them causes, during peptide coupling reactions, problems of regioselectivity as well as parasitic reactions and undesirable molecular rearrangements.

To eliminate these disadvantages, it is necessary that at least one of the two nitrogen atoms of the hydrazino acid is temporarily neutralized with a protecting group PG.

In the documents [Tetrahedron Lett. 32, 2765 (1991); J. Prakt. Chem. 314, 735 (1972); J. Prakt. Chem. 316, 729 (1974); J. Prakt. Chem. 314, 751 (1972)], a PG group was directly introduced into an α-hydrazino acid, and a mixture of Nα- and Nβ-protected products is most often obtained which should then be separated and purified.

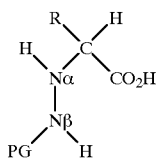 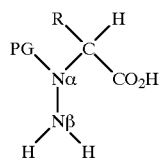

The inventors have described, in the documents [J. Chem. Soc., Chem. Commun. 435 (1991); J. Org. Chem. 58, 4791 (1993)] how the Nβ-protected compounds can be exclusively prepared using electrophilic amination of an amino acid with an oxaziridine. In the case where PG is Boc (tert-butoxycarbonyl), this method gives poor yields because of the formation of oxazolidinone which is produced at the expense of the desired product during the isolation. The yields are better if PG is Moc (methoxycarbonyl) but this group is cleaved under excessively harsh conditions which are incompatible with peptide synthesis.

In the document [Tetrahedron 44, 5525 (1988)], the preparation of compounds carrying two identical protecting groups (Boc) on the Nα and Nβ nitrogens is described. In the document [New. J. Chem. 13, 849 (1989)], one of the co-inventors uses the acetyl (Ac) radical to protect the two nitrogens.

The compounds of general formula

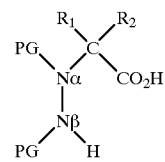

in which the two protecting groups PG are identical are not easy to use in peptide synthesis, on the one hand because these groups cannot be selectively cleaved in relation to one another (thus liberating the two nitrogenous groups) and, on the other hand, as regards the Ac group, because its cleavage requires drastic conditions which are incompatible with peptide synthesis.

In the documents [J. Prakt. Chem. 314, 735 (1972); Chem. Ber. 99, 3914 (1966); Tetrahedron Lett. 31, 2701 (1975); Japanese Patent 76138602-761130 (1976); Tetrahedron Lett. 34, 6859 (1993)], there are described compounds of general formula

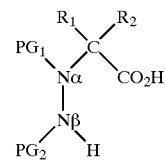

carrying two different protecting groups $PG_1$ and $PG_2$. However, while one of the groups proposed is standard (Boc, Z (benzyloxycarbonyl), or benzyl) the other (Ac or Tos) is unsuitable for peptide synthesis because of the drastic conditions necessary for its cleavage.

The invention overcomes these disadvantages. It relates, by way of new industrial products, to hydrazino acid derivatives in which the two amine functional groups carry orthogonal protecting groups, that is to say which can be manipulated independently of one another, for example during a peptide synthesis.

BRIEF DESCRIPTION OF THE INVENTION

The invention relates, by way of new industrial products, to hydrazino acid derivatives of general formula:

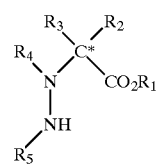

in which:

$R_1$, $R_2$ and $R_3$ denote hydrogen or a carbonaceous radical, while $R_2$ and $R_3$ are different, C* denotes an asymmetric carbon of L, D or DL configuration, $R_4$ and $R_5$ denote a protecting group, wherein:

$R_4$ denotes a benzyl radical $ArCH_2$ of formula:

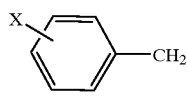

where Ar denotes a phenyl radical or a phenyl radical substituted with one or more groups X;

where X denotes hydrogen, a halogen, a nitro radical or an alkyl radical;

and $R_5$ denotes a group Y—O—CO, in which Y denotes a carbonaceous radical different from $R_4$.

In other words, the invention relates to α-hydrazino acids in which the two nitrogenous groups Nα and Nβ carry protecting groups which are different in nature, in particular benzyl ($PhCH_2$) on the Nα, and tert-butoxycarbonyl (Boc) or fluorenylmethoxycarbonyl (Fmoc) on the Nβ, groups whose orthogonal character makes it possible to manipulate them independently of one another.

These compounds can be directly used in the syntheses of pseudopeptides by conventional solid phase or liquid phase methods, and can also be used in the context of methods of combinatory synthesis currently in rapid development.

Advantageously, in practice:

$R_1$ is hydrogen or an alkyl or benzyl group;

$R_2$ denotes hydrogen or an alkyl group;

$R_3$ denotes hydrogen or a side chain (optionally protected) of natural proteogenic amino acids, an aromatic group such as phenyl or para-hydroxyphenyl, a primary, secondary or tertiary alkyl.

Preferably, $R_3$ denotes, in addition to hydrogen, the side chains (optionally protected) of proteogenic amino acids, that is to say pure enantiomers of the L series, as well as their antipodes of the D series and the racemic mixtures or partially resolved DL mixtures.

Advantageously, according to the invention, in the protecting group $R_4$ linked to the Na nitrogen, X is equal to H.

Likewise, still according to the invention, in the protecting group $R_5$ linked to the terminal Nβ nitrogen, Y is advantageously the tert-butyl group (Y—O—CO is Boc) or the 9-fluorenylmethyl group (Y—O—CO is Fmoc).

The invention also relates to a process for the preparation of these compounds.

Advantageously, the compounds for which $R_5$ is Boc or Fmoc are obtained directly by reacting the corresponding N-benzylated α-amino acids (whose preparation is trivial) with an aminating oxaziridine, whose nitrogen carries a Boc or Fmoc group, following the examples described by the authors in the following documents [J. Org. Chem. 58, 4791 (1993); Tetrahedron Lett. 36, 1439 (1995)].

In this reaction, the entire N-Boc (or N-Fmoc) fragment of oxaziridine is transferred onto the N-benzylated α-amino acid to give the desired compound. The reaction is carried out in dichloromethane (or in other solvents such as ether or chloroform) at a temperature between −20° C. and +20° C. depending on the cases (most of them 0° C.).

Among the major characteristics of the reaction, the following should be noted:

a) the N-benzylated α-amino acid, which is prepared by conventional methods, is made soluble in the reaction solvent by in situ conversion to a quaternary ammonium salt (e.g. tetraethylammonium salt) or, in some cases, to an alkali metal salt (e.g. sodium salt);

b) Examples 1 to 11 described below use, as amination reagent, N-Boc-3-(4-cyanophenyl)oxaziridine (or BCPO), to give the desired compounds with $R_5$=Boc. Other oxaziridines of the same family can be used, in particular N-Boc-3-(2,4-dichlorophenyl)oxaziridine which is less expensive;

c) the compounds in which $R_5$ is Fmoc can be obtained in a manner similar to those where $R_5$ is Boc, using N-Fmoc-3-phenyloxaziridine; more advantageously, they can be prepared indirectly from the compounds where $R_5$ is Boc by deprotection of the Nβ followed by reprotection with Fmoc-Cl (see Example 12 below);

d) the N-benzylated α-amino acids of the L series give the desired compounds of the same L configuration with conservation of the enantiomeric purity. The N-benzylated α-amino acids of the D series similarly give the desired compounds of the D series, and the N-benzylated DL α-amino acids (racemates) similarly give the racemic compounds;

e) some compounds whose physical characteristics may be unfavorable (hygroscopicity) are conveniently isolated in the form of amine salts (for example dicyclohexylamine salts).

The manner in which the invention can be carried out and the advantages resulting therefrom will emerge more clearly from the exemplary embodiments which follow.

Ways of Carrying out the Invention

One mmol of N-benzylated amino acid is placed in a 10 ml round-bottomed flask, followed by 0.667 ml (1 mmol) of a 1.5 M methanolic solution of tetraethylammonium hydroxide. The mixture is left for about 15 min at room temperature, with stirring, until the solution becomes clear. The methanol is evaporated and replaced with 3 ml of dichloromethane. 246 mg of N-tert-butoxycarbonyl-3-(4-cyanophenyl)oxaziridine (1 mmol), dissolved in 2 ml of dichloromethane, are added dropwise to this solution, cooled to 0° C. on an ice bath. The round-bottomed flask is hermetically sealed and is placed in a refrigerator for 12 hours.

Treatment

The solvent is evaporated, and the oily residue is taken up in 50 ml of water containing 12 mg of sodium hydroxide (0.3 mmol). After stirring for 30 min, a para-cyanobenzaldehyde precipitate is formed which is separated by filtration. The remaining aqueous phase is salified and washed with seven times 10 ml of ether, and then acidified to pH 3 with 177 mg of potassium hydrogen sulfate (1.3 mmol). A milky phase is obtained which is extracted with twice 20 ml of dichloromethane (or ether). After drying over sodium sulfate and evaporation of the solvent, the desired product is obtained, most often in the form of a solid whose chemical purity is very good. In some cases, the product may be recrystallized from an appropriate solvent (e.g. pentane/isopropyl ether mixtures). Some products were also isolated in the form of amine or sodium salts.

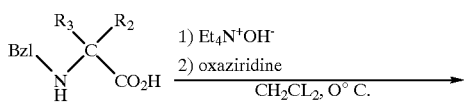

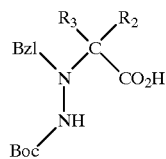

EXAMPLE 1

Preparation of $N^\alpha$-benzyl-$N^\beta$-Boc-(L)-hydrazinoalanine (1a)

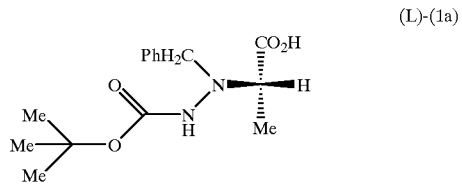

According to the typical procedure, 1.435 g of N-benzyl-(L)-alanine (8 mmol) give 2.09 g (88%) of solid compound (1a). *Physical characteristics*: m.p. 117° C.; $[\alpha]_D^{25}$+22.8 (c 1.14; MeOH); NMR (CDCl$_3$) δ: 1.32 (s, 9H, Boc) 1.38 (d, J=7 Hz, 3H, Me) 3.64 (q, J=7 Hz, 1H, CH$^\alpha$) 3.95 (s, 2H, CH$_2$ Bzl) 5.85 (s, 1H, NH) 7.26–7.36 (m, 5H, arom). The dicyclohexylamine salt of (1a) has a melting point m.p. 170° C. (decomposition), and a specific rotation $[\alpha]_D^{25}$+43.7 (c=1.33; MeOH). NMR (CDCl$_3$) δ: 1.22–1.67 (m, 24H, Boc+Cy+Me) 1.79 (m, 4H, Cy) 2.02 (m, 4H, Cy) 2.93 (m, 2H, Cy) 3.38 (q, J=7 Hz, 1H, CH$^\alpha$) 4.01 (s, 2H, CH$_2$ Bzl) 7.23 and 7.39 (m, 5H, arom) Cy=cyclohexyl. *Elemental analysis* [$C_{15}H_{22}N_2O_4$+$C_{12}H_{23}N$+0.25 $H_2O$], calc (%) C 67.54; H 9.55; N 8.75; found C 67.30; H 9.52; N 8.67.

EXAMPLE 2

Preparation of Nα-benzyl-Nβ-Boc-(L)-hydrazinovaline (1b)

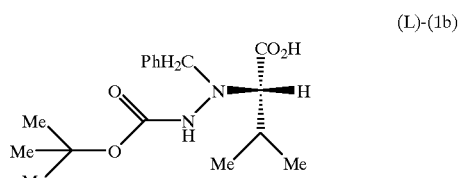

According to the typical procedure, starting with 207 mg (1 mmol) of N-benzyl-(L)-valine, 220 mg (68%) of (1b) are obtained in the form of a solid, m.p. 117° C. (decomposition), $[\alpha]_D^{25}$+25.6 (c=1.19; MeOH). NMR (CDCl$_3$) δ: 0.96 (d, J=7 Hz, 3H, Me) 1.08 (d, J=7 Hz, 3H, Me) 1.36 (s, 9H, Boc) 2.09 (m, 1H, CH$^\beta$) 3.11 (sl, 1H, CH$^\alpha$) 3.91 (m, 2H, CH$_2$ Bzl) 7.24–7.37 (m, 5H, arom) 10.21 (sl, 1H, CO$_2$H). Elemental analysis $C_{17}H_{26}N_2O_4$ calc (%) C 63.33; H 8.13; N 8.69; found C 63.23; H 8.10; N 8.70.

EXAMPLE 3

Preparation of $N^\alpha$-benzyl-$N^\beta$-Boc-(L)-hydrazinoisoleucine (1c)

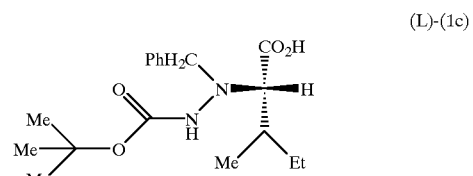

According to the typical procedure, starting with 222 mg (1 mmol) of N-benzyl-(L)-isoleucine, 260 mg (78%) of (1c) are obtained in the form of a solid, m.p. 108° C. (decomposition); $[\alpha]_D^{25}$+32.7 (c=1.00; MeOH); NMR (CDCl$_3$) δ: 0.83 (t, J=7 Hz, 3H, Me$^\delta$) 0.92 (d, J=7 Hz, 3H, Me) 1.35 (m, 10H, Boc+CH$^\gamma$) 1.86 (m, 2H, CH$^\beta$+CH$^\gamma$) 3.23 (sl, 1H, CH$^\alpha$) 3.91 (m, 2H, CH$_2$ Bzl) 7.24–7.35 (m, 5H, arom). Elemental analysis $C_{18}H_{28}N_2O_4$ calc. (%) C 64.26; H 8.39; N 8.33; found C 64.18; H 8.34; N 8.54.

EXAMPLE 4

Preparation of $N^\alpha$-benzyl-$N^\beta$-Boc-(L)-hydrazinoserine (1d)

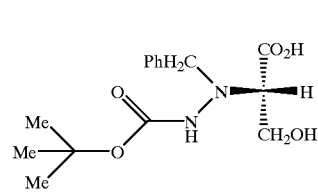

The typical procedure is followed, starting with 195 mg (1 mmol) of N-benzyl-(L)-serine. 210 mg (68%) of (1d) are obtained. Solid, m.p. 141° C. (decomposition); $[\alpha]_D^{25}$+9.0 (c=1.07; MEOH); NMR (CDCl$_3$) δ: 1.30 (s, 9H, Boc) 3.78–4.13 (m, 5H, CH$_2^\beta$+CH$^\alpha$+CH$_2$ Bzl) 6.37 (s, 1H, NH) 7.24–7.36 (m, 5H, arom). Elemental analysis [$C_{15}H_{22}N_2O_5$+ 0.25 $H_2O$] calc. (%) C 57.22; H 7.20; N 8.90; found C 57.02; H 6.94; N 8.80.

EXAMPLE 5

Preparation of $N^\alpha$-benzyl-$N^\beta$-Boc-(L)-hydrazinoasparagine (1e)

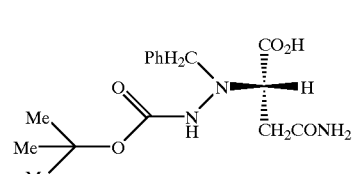

According to the typical procedure, starting with 444 mg (2 mmol) of N-benzyl-(L)-asparagine, 440 mg (65%) of (1e) are obtained. m.p. 189° C. (decomposition); $[\alpha]_D^{25}$ −17.2 (c=1.10; MeOH); NMR (CDCl$_3$) δ: 1.28 (s, 9H, Boc) 2.70 (d, J=7 Hz, 2H, CH$_2^\beta$) 3.82 (t,=7 Hz, 1H, CH$^\alpha$) 4.09 (q, J=8 Hz, 2H, CH$_2$ Bzl) 6.22 and 6.67 (s, 2H, NH$_2$) 7.24–7.32 (m, 5H, arom). Elemental analysis C$_{16}$H$_{23}$N$_3$O$_5$ calc. (%) C 56.96; H 6.87; N 12.46; found C 56.75; H 7.09; N 12.28.

EXAMPLE 6

Preparation of N$^\alpha$-benzyl-N$^\beta$-Boc-(L)-hydrazinotryptophan (1f)

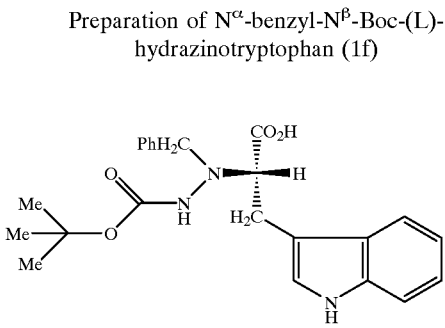

(L)-(1f)

According to the typical procedure, 588 mg (2 mmol) of N-benzyl-(L)-trytophan give 670 mg (80%) of (1f), solid decomposing upon heating; $[\alpha]_D^{25}$ +1.6 (c=1.17; MeOH); NMR (CDCl$_3$) δ: 1.37 (s, 9H, Boc) 3.23–3.54 (m, 2H, CH$_2^\beta$) 3.81 and 4.01 (m, 3H, CH$^\alpha$+CH$_2$ Bzl) 6.45 (sl, 1H, NH) 7.07–7.57 (m, 10H, arom) 8.42 (sl, 1H, NH indole) 10.15 (sl, 1H, CO$_2$H). Elemental analysis [C$_{23}$H$_{27}$N$_3$O$_4$+0.25 H$_2$O] calc. (%) C 66.73; H 6.70; N 10.15; found C 67.00; H 6.83; N 9.83.

EXAMPLE 7

Preparation of benzyl N$^\alpha$-benzyl-N$^\beta$-Boc-(L)-hydrazinoaspartate (1g)

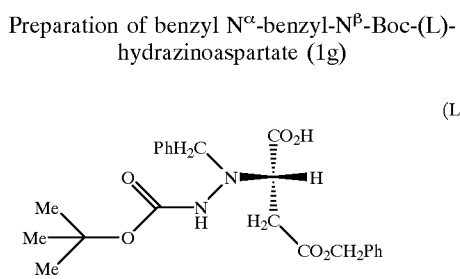

(L)-(1g)

According to the typical procedure, 313 mg (1 mmol) of benzyl N$^\alpha$-benzyl-β-(L)-aspartate give 318 mg (75%) of (1g). Solid decomposing at 113° C.; $[\alpha]_D^{25}$ −4.2 (c=0.98; MeOH); NMR (CDCl$_3$) β: 1.26 (s, 9H, Boc) 2.86 (m, 2H, CH$_2^\beta$) 3.90 and 4.02 (m, 3H, CH$^\alpha$+CH$_2$ Bzl) 5.14 (s, 2H, OCH$_2$) 6.15 (sl, 1H, NH) 7.25 (s, 5H, arom) 7.32 (s, 5H, arom). Elemental analysis C$_{23}$H$_{28}$N$_2$O$_6$ calc. (%) C 64.47; H 6.59; N 6.54; found C 64.31; H 6.58; N 6.58.

EXAMPLE 8

Preparation of N$^\alpha$-benzyl-N$^\beta$-Boc-N$^\epsilon$-Z-(L)-hydrazinolysine (1h)

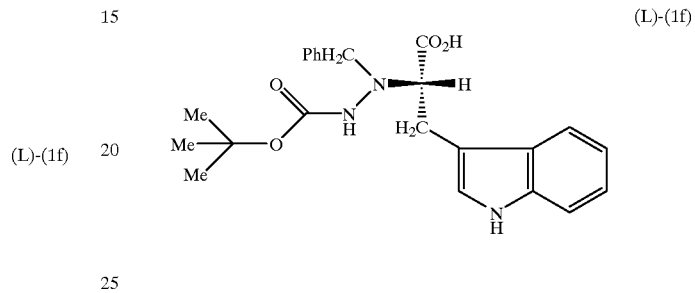

(L)-(1f)

According to the typical procedure, 375 mg (1 mmol) of N$^\alpha$-benzyl-N$^\epsilon$-carbobenzoxy-(L)-lysine lead to the isolation of (1h) in the form of a hygroscopic oil which is converted to its sodium salt by treating with 1.5 mmol of NaOH in 5 ml of water. After freeze-drying, 365 mg (72%) of the sodium salt of (1h) are obtained. $[\alpha]_D^{25}$ +35.1 (c=0.99; MeOH); NMR (D$_2$O) δ: 0.98 and 1.10 (s, 9H, Boc) 1.32 (m, 4H, CH$_2^{\gamma\delta}$) 1.49 (m, 2H, CH$_2^\beta$) 2.97 (m, 2H, CH$_2^\epsilon$) 3.12 (m, 1H, CH$^\alpha$) 3.66 (m, 2H, CH$_2$ Bzl) 4.96 (s, 2H, OCH$_2$) 7.24 (s, 5H, arom) 7.28 (s, 5H, arom).

EXAMPLE 9

Preparation of N$^\alpha$-benzyl-N$^\beta$-Boc-(L)-hydrazinomethionine-S-oxide (1i)

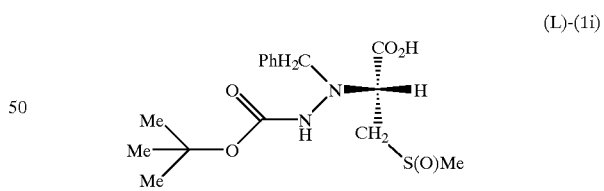

(L)-(1i)

According to the typical procedure, starting with 255 mg (1 mmol) of N-benzyl-(L)-methionine sulfoxide, 281 mg (76%) of the compound (1i) are obtained. Solid decomposing upon heating; $[\alpha]_D^{25}$ +9.7 (c=1.03; MeOH); NMR (CDCl$_3$) δ: 1.33 (s, 9H, Boc) 2.08–2.28 (m, 2H, CH$_2^\beta$) 2.59 and 2.62 (s, 3H, SOMe) 3.10 (m, 1H, CH$^\alpha$) 3.44 (m, 2H, CH$^\gamma$) 4.02 (m, 2H, CH$_2$ Bzl) 6.86 (sl, 1H, NH) 7.24–7.34 (m, 5H, arom). Elemental analysis C$_{17}$H$_{26}$N2O$_5$S calc. (%) C 55.12; H 7.07; N 7.56; S 8.65; found C 54.87; H 7.00; N 7.84; S 8.22.

EXAMPLE 10

Preparation of $N^\alpha$-benzyl-$N^\beta$-Boc-O-benzyl-(L)-hydrazinotyrosine (1j)

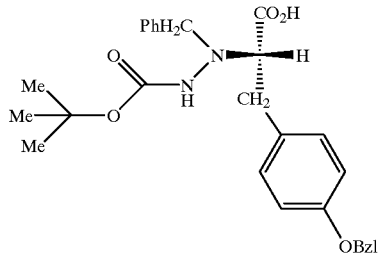

(L)-(1j)

According to the typical procedure, starting with 366 mg (1 mmol) of $N^\alpha$-benzyl-(L)-tyrosine benzyl ether, 250 mg (52%) of (1j) are obtained. Solid decomposing upon heating; $[\alpha]_D^{25}$+13.3 (c=1.35; MeOH); NMR (CDCl$_3$) δ: 1.33 (s, 9H, Boc) 2.98 and 3.29 (m, 2H, CH$_2^\beta$) 3.70 and 3.83 (m, 3H, CH$^\alpha$+CH$_2$ Bzl) 5.06 (s, 2H, OCH$_2$) 5.88 (sl, 1H, NH) 6.94 (m, 2H, arom) 7.17–7.41 (m, 12H, arom). Elemental analysis [C$_{28}$H$_{32}$N2O$_5$+0.25 H$_2$O] calc. (%) C 69.91; H 6.81; N 5.82; found C 69.79; H 6.92; N 5.83.

EXAMPLE 11

Preparation of $N^\alpha$-benzyl-$N^{im}$-benzyl-$N^\beta$-Boc-(L)-hydrazinohistidine (1k)

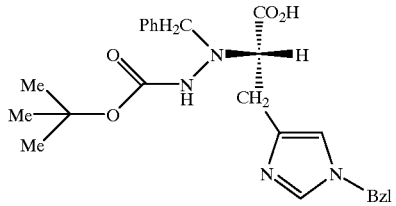

(L)-(1k)

According to the typical procedure, starting with 359 mg (1 mmol) of $N^\alpha$-benzyl-$N^{im}$-benzyl-(L)-histidine, 338 mg (75%) of (1k) are obtained in the form of a yellow oil which solidifies in pentane. $[\alpha]_D^{25}$-34.2 (c=1.33; MeOH); NMR (CDCl$_3$) δ: 1.31 (s, 9H, Boc) 3.07 (m, 2H, CH$_2^\beta$) 3.55 (m, 3H, CH$^\alpha$)+3.97 (m, 2H, CH$_2$ Bzl) 5.08 (m, 2H, CH$_2$ Bzl imidazole) 6.96–7.34 (m, 12H, arom). Elemental analysis [C$_{34}$H$_{41}$N$_5$O$_8$+0.75 H$_2$O] calc. (%) C 64.71; H 6.84; N 12.07; found C 64.67; H 6.87; N 11.92.

EXAMPLE 12

Preparation of $N^\alpha$-benzyl-$N^\beta$-Fmoc-(L)-hydrazinoalanine (2)

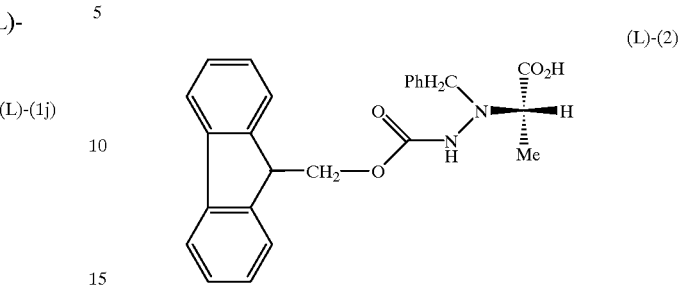

(L)-(2)

164 mg (0.556 mmol) of $N^\alpha$-benzyl-$N^\beta$-Boc-(L)-hydrazinoalanine are treated with 1 ml of a 3 M solution of hydrogen chloride in ethyl acetate. After stirring for 2 hours at room temperature, the mixture is carefully concentrated under vacuum and then taken up in 1.45 ml of water and 0.6 ml of dioxane. It is treated at 0° C. with 554 mg (1.93 mmol) of sodium carbonate decahydrate and then with 156 mg (0.58 mmol) of 97% 9-fluorenylmethyl chloroformate. The mixture is then stirred overnight at room temperature. The reaction mixture is filtered and the solid washed with 2 ml of a mixture of water and dioxane. The filtrate is concentrated and then taken up in 15 ml of a 10% NaCl solution. The aqueous phase is washed twice with 10 ml of ether and then acidified to pH 3 with 6 M hydrochloric acid. After extracting with twice 10 ml of ether, drying the organic phase over Na$_2$SO$_4$ and evaporating, 140 mg (61%) of $N^\alpha$-benzyl-$N^\beta$-Fmoc-(L)-hydrazinoalanine are recovered in the form of a pure whitish solid by TLC. Physical characteristics. Decomp. towards 60° C.; $[\alpha]_D^{25}$13.9 (c=0.5, MeOH); $^1$H NMR (DMSO-d6) δ: 1.03 (d, 3H, CH3, J=5.8 Hz); 3.47–4.37 (m, 6H); 7.20–7.89 (m, 13H); 8.17 (s, 1H, NH); 12.54 (s, 1H, CO$_2$H). Elemental analysis C$_{25}$H$_{24}$N$_2$O$_4$.

The preparation of hydrazino peptides from the protected hydrazino acids of Examples 1 and 3 will now be described.

EXAMPLE 13

Preparation of Boc(Bzl)hAlaAlaNHiPr (3)

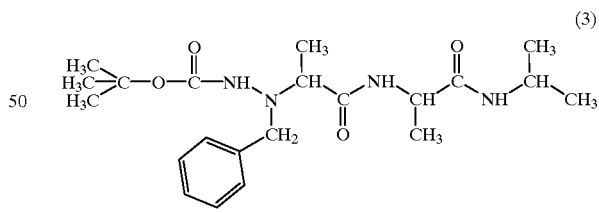

(3)

1) Preparation of the activated ester. Boc(Bzl)hAla (0.5 mmol, 151 mg) is placed at 0° C. in 0.5 ml of dry DMF in the presence of DCC (0.5 mmol, 103 mg) and pentafluorophenol (0.5 mmol, 92 mg). The reaction medium is stirred for 15 hours in a refrigerator.

2) Coupling. The above activated ester solution is filtered directly over HAlaNHiPr (0.5 mmol, 65 mg), the filtered DCU is rinsed with 0.1 ml of DMF and then the medium is stirred for 24 hours at room temperature. After evaporation of the DMF, the crude product is taken up in 2 ml of CH$_2$Cl$_2$ and washed with three times 2 ml of water. The organic phase is dried, evaporated and the residue chromatographed on a column of 5 g of silica (eluent $CH_2Cl_2$/MeOH 50/50). 136 mg (67%) of a pure fraction of the protected hydrazino dipeptide Boc(Bzl)hAlaAlaNHiPr (3) are recovered. $[\alpha]_D^{25}$ −21.1 (c=1; $CH_2Cl_2$); NMR ($CDCl_3$) δ: 1.0 to 1.22 (m, 21H, $CH_3$ BOC+$CH_3$ Ala +$CH_3$ iPr) 3.87 (s, 2H, $CH_2$—Ph) 3.97 (q, J=6.8 Hz, 1H, NH—N(Bzl)—C$\underline{H}$—) 4.32 (m, 1H, CHα Ala) 6.19 (d, J=7.4 Hz, 1H, NH) 7.30 (m, 5H, Ph) 8.43 (s, 1H, NH). Elemental analysis [$C_{21}H_{34}N_4O_4$+ 0.75 $H_2O$] calc (%) C 60.00; H 8.51; N 13.34; found C 59.91; H 8.11; N 13.22.

EXAMPLE 14

Preparation of BocVal(Bzl)hAlaAlaNHiPr (4)

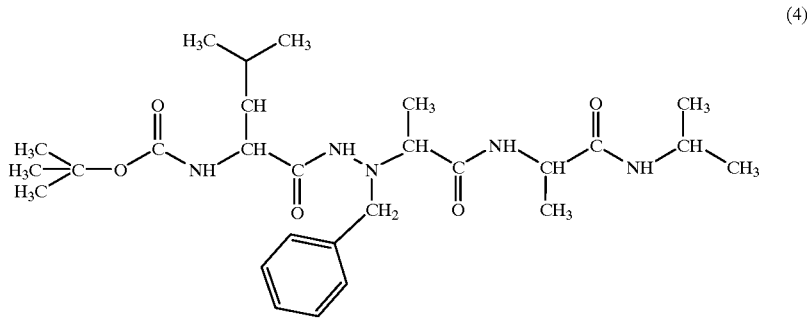

(4)

BocValNCA (0.46 mmol, 99 mg) is placed in 1 ml of dry THF under argon at room temperature. The (Bzl) hAlaAlaNHiPr hydrochloride (0.46 mmol, 155 mg) obtained by treating Boc(Bzl)hAlaAlaNHiPr (0.46 mmol, 193 mg) with 3 M HCl in ethyl acetate overnight followed by evaporation is added in solution in 5 ml of dry THF, in the presence of triethylamine dried on a sieve (0.46 mmol, 64 μl). The mixture is stirred for 2 hours at room temperature. After evaporation of the THF, the residue is taken up in 5 ml of $CH_2Cl_2$ and then washed with 5 ml of water, and 5 ml of a 5% $KHCO_3$ solution. 225 mg of product are obtained after drying and evaporation, which product is purified by chromatography on a column of 7 g of silica (eluent $CH_2Cl_2$/ MeOH 95/5). 140 mg (60%) of pure product (4) are recovered in the form of a white powder. $[\alpha]_D^{25}$ +1.3 (c=0.75; $CH_2Cl_2$); NMR (DMSO) δ: 0.56 (d, J=6.5 Hz, 3H, $CH_3$ iPr or $CH_3$ Val) 0.66 (d, J=6.5 Hz, 3H, $CH_3$ iPr or $CH_3$ Val) 1.0 (d, J=6.5 Hz, 3H, $CH_3$ iPr or $CH_3$ Val) 1.04 (d, J=6.5 Hz, 3H, $CH_3$ iPr or $CH_3$ Val) 1.34 (s, 9H, $CH_3$ Boc) 1.45 (d, J=6.4 Hz, 3H, $CH_3$ Ala) 1.66 (m, 1H, CHβ Val) 1.75 (d, J=6 Hz, 3H, $CH_3$ Ala) 3.3 to 3.6 (m, 2H, CHα) 4.18 (m, 1H, CHα) 4.85 (m, 3H, $CH_2$—Ph+CHα) 6.58 (d, J=8.4 Hz, 1H, NH-Boc) 7.3 (m, 5H, Ph) 7.66 (d, J=8 Hz, 1H, NH Ala or NH-iPr) 8.46 (d, J=8 Hz, 1H, NH Ala or NH-iPr) 8.97 (s, 1H, NH-N). Elemental analysis [$C_{26}H_{43}N_5O_5$+1 $H_2O$] calc. (%) C 59.74; H 8.57; N 13.39; found C 59.50; H 8.57; N 12.91.

EXAMPLE 15

Preparation of Boc(Bzl)hIleLeuOMe (5)

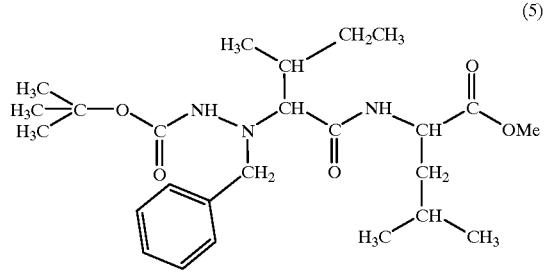

(5)

A mixture of 84.1 mg (0.25 mmol) of Boc(Bzl)hIle and of 54.5 mg (0.30 mmol) of LeuOMe hydrochloride in solution in 0.5 ml of methylene chloride is treated at 0° C. with 130 mg (0.25 mmol) of PyBop and then with 105 μl of triethylamine (0.75 mmol). The mixture is stirred for 10 minutes at 0° C. and then maintained at room temperature overnight. After evaporation of the solvent and chromatography on 10 g of silica gel (eluent $CH_2Cl_2$/MeOH 98/2), 83.4 mg (72%) of dipeptide Boc(Bzl)hIleLeuOMe (5) are isolated, which dipeptide crystallizes after a few weeks. m.p. 74° C.; $[\alpha]_D^{25}$ +13.9 (c=1; MeOH); NMR (DMSO) δ: 0.76–0.93 (m, 12H, $CH_3$) 1.19–1.28 (m, 10H, Boc and CH) 1.45–1.91 (m, 5H, CH Ile and Leu) 3.03 (d, 1H, CHα hIle, J=8.7 Hz) 3.61 (s, 3H, OMe) μ3.77 (broad s, 2H, $CH_2$Ph) 4.35 (broad s, 1H, CHα Leu) 7.06–7.32 (m, 5H, Ph) 7.70 (broad s, 1H, NHBoc) 8.57 (d, 1H, NH, J=6.5 Hz). Elemental analysis $C_{25}H_{41}N_3O_5$ calc. (%) C 64.77; H 8.91; N 9.06; found C 64.61; H 8.96; N 9.09.

EXAMPLE 16

Preparation of BocValhIleLeuOMe (6)

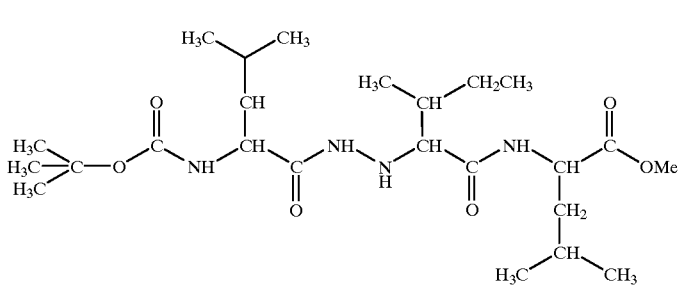

1) Deprotection of (6). A suspension of 5 mg of 5% palladium on carbon and 80 mg (0.172 mmol) of Boc(Bzl) hIleLeuOMe (5) in 2 ml of methanol is hydrogenated at atmospheric pressure for 1 hour. The product obtained after filtration on celite and then concentration is then treated with 0.5 ml of 3 M HCl in ethyl acetate overnight, to give after concentration 54 mg (100%) of hIleLeuOMe hydrochloride.

2) Coupling. A solution, brought to −15° C., of 37.7 mg of BocVal in 1 ml of anhydrous THF is treated with 19 μl (0.172 mmol) of N-methylmorpholine and then with 22 μl of isobutyl chloroformate. After stirring for 3 minutes, a solution of 54 mg of hIleLeuOMe hydrochloride, 20 μl of N-methylmorpholine in 0.5 ml of anhydrous DMF is introduced. The temperature is allowed to rise slowly and after overnight storage, the mixture is concentrated. The residue is taken up in 15 ml of dichloromethane and then washed with 10% sodium hydrogen sulfate, with 10% sodium hydrogen carbonate and then with water. After drying over sodium sulfate, concentration and chromatography on 2.5 g of silica (eluent $CH_2Cl_2/Et_2O$ 80/20), 54 mg (67%) of BocValhIleLeuOMe (6) are isolated in the form of a white solid. $[\alpha]_D^{25}$−69.9 (c=0.6; MeOH); NMR (DMSO) δ: 0.77–0.90 (m, 18H, $CH_3$) 1.19 (m, 2H, CH) 1.36 (s, 9H, Boc) 1.47–1.85 (m, 5H, CH Ile, Val and Leu) 3.22 (dd, 1H, CHα hIle, J=4.2 Hz) 3.59 (s, 3H, OMe) 3.71 (m, 1H, CHα Val) 4.25 (broad s, 1H, CHα Leu) 5.00 (broad s, 1H, NHα) 6.52 (d, 1H, NH Val, J=8.8 Hz) 8.15 (d, 1H, NH Leu, J=7.3 Hz) 9.12 (broad s, 1H, NH hIle). Elemental analysis $C_{23}H_{44}N_4O_6$ calc (%) C 58.45; H 9.38; N 11.85; found C 58.10; H 9.37; N 11.60.

The new compounds in accordance with the invention are characterized in that they comprise orthogonal protecting groups, and can thus be used as synthons for the preparation of a new class of pseudopeptides of therapeutic value, without modifying the techniques for peptide synthesis in use, in particular in automatic synthesizers.

As already stated, their preparation is easy from simple amino acid derivatives. Some of the oxaziridines which can be used for their synthesis are themselves accessible by viable economic routes.

The generalization of the invention as a new method of obtaining enantiomerically pure or racemic α-hydrazino acids, by simply cleaving the two protecting groups $R_4$ and $R_5$ is of great interest, because it makes it possible to easily obtain such compounds with a wide variety of side chains. The corresponding α-amino acids simply have to be available.

To summarize, these synthons can be advantageously used for:

the synthesis of pseudopeptides of the hydrazino peptide or N-amino peptide family by common methods using the Boc or Fmoc methodologies, including in automatic synthesizers;

the combinatory synthesis of pseudopeptides;

the synthesis of L, D or DL a-hydrazino acids.

We claim:

1. An α-hydrazino acid derivative of general formula:

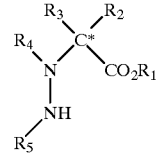

in which:

$R_1$, $R_2$ and $R_3$ denote hydrogen or a radical comprising at least one carbon atom, while $R_2$ and $R_3$ are different, C* denotes an asymmetric carbon of L, D or DL configuration, $R_4$ and $R_5$ denote a protecting group, wherein:

$R_4$ denotes a benzyl radical $ArCH_2$ of formula:

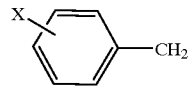

where Ar denotes a phenyl radical or a phenyl radical substituted with one or more groups X;

where X denotes hydrogen, a halogen, a nitro radical or an alkyl radical;

and $R_5$ denotes a tert-butoxycarbonyl (Boc).

2. The α-hydrazino acid derivative as claimed in claim 1, wherein:

$R_1$ is hydrogen or an alkyl or benzyl group;

$R_2$ denotes hydrogen or an alkyl group;

$R_3$ denotes hydrogen or a side chain protected or otherwise of natural proteogenic amino acids, or an aromatic group.

3. The α-hydrazino acid derivative as claimed in claim 1 wherein $R_3$ denotes a phenyl or para-hydroxyphenyl, or a primary secondary or tertiary alcohol.

4. The α-hydrazino acid derivative as claimed in claim 1, wherein $R_3$ is a side chain protected or otherwise of proteogenic amino acids.

5. An α-hydrazino acid derivative of general formula:

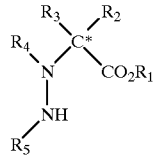

in which:

$R_1$, $R_2$ and $R_3$ denote hydrogen or a radical comprising at least one carbon atom, while $R_2$ and $R_3$ are different, C* denotes an asymmetric carbon of L, D or DL configuration, $R_4$ and $R_5$ denote a protecting group, wherein:

$R_4$ denotes a benzyl radical $ArCH_2$ of formula:

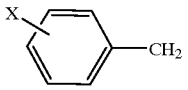

where Ar denotes a phenyl radical or a phenyl radical substituted with one or more groups X;

where X denotes hydrogen, a halogen, a nitro radical or an alkyl radical;

and $R_5$ denotes a 9-fluorenylmethoxycarbonyl (Fmoc).

6. The α-hydrazino acid derivative as claimed in claim 5, wherein:

$R_1$ is hydrogen or an alkyl or benzyl group;

$R_2$ denotes hydrogen or an alkyl group;

$R_3$ denotes hydrogen or a side chain protected or otherwise of natural proteogenic amino acids, or an aromatic group.

7. The α-hydrazino acid derivative as claimed in claim 5, wherein $R_3$ denotes a phenyl or para-hydroxyphenyl, or a primary secondary or tertiary alcohol.

8. The α-hydrazino acid derivative as claimed in claim 5, wherein $R_3$ is a side chain protected or otherwise of proteogenic amino acids.

* * * * *

UNITED STATES PATENT AND TRADEMARK OFFICE
CERTIFICATE OF CORRECTION

PATENT NO. : 5,962,722
DATED : October 5, 1999
INVENTOR(S) : Andre Collet etal.

It is certified that error appears in the above—identified patent and that said Letters Patent is hereby corrected as shown below:

On title page, item

[22] Please delete the incorrect date of [April 4, 1996] in favor of

--September 4, 1996--.

Signed and Sealed this

Eighteenth Day of April, 2000

*Attest:*

Q. TODD DICKINSON

*Attesting Officer*      *Director of Patents and Trademarks*